United States Patent
Reckziegel et al.

(10) Patent No.: US 7,884,065 B2
(45) Date of Patent: Feb. 8, 2011

(54) 4-ISOAMYLCYCLOHEXANOL AS ODIFERANT

(75) Inventors: Aurelia Reckziegel, Dormagen (DE); Horst Surburg, Holzminden (DE); Erich Dilk, Holzminden (DE)

(73) Assignee: Symrise AG, Holzminden (DE)

( * ) Notice: Subject to any disclaimer, the term of this patent is extended or adjusted under 35 U.S.C. 154(b) by 984 days.

(21) Appl. No.: 11/576,268

(22) PCT Filed: Sep. 26, 2005

(86) PCT No.: PCT/EP2005/054810

§ 371 (c)(1), (2), (4) Date: Mar. 29, 2007

(87) PCT Pub. No.: WO2006/035010

PCT Pub. Date: Apr. 6, 2006

(65) Prior Publication Data

US 2010/0130397 A1     May 27, 2010

(30) Foreign Application Priority Data

Sep. 30, 2004   (DE) ................. 10 2004 047 536

(51) Int. Cl.
*A61K 8/00*    (2006.01)

(52) U.S. Cl. ........................... 512/23; 510/106
(58) Field of Classification Search ................. 568/832; 512/23; 510/106
See application file for complete search history.

(56) References Cited

U.S. PATENT DOCUMENTS 4,400,545 A     8/1983   Willis

OTHER PUBLICATIONS

David, S. and Imer, C.: "Contributiona l'étude des constituants du houblon (Partie I)", Bulletin de la Societe Chimique de France, 1951, Seiten 634-637, XP002356398.
Parkhi, S.: "Synthesis of a completely reduced analogue of hexestrol, 1:2-diethyl-1-(4-methoxycyclohexyl)-2-(4-isoamyl-cyclohexyl)-ethane", Journal Indian Chemical Society, 1956, Seiten 313-317, XP008056361.

*Primary Examiner*—John R Hardee
(74) *Attorney, Agent, or Firm*—Duane Morris LLP; Gregory M. Lefkowitz

(57) ABSTRACT

The use of 4-isoamylcyclohexanol [4-(3-methylbutyl)-cyclohexan-1-ol], in particular of cis-4-isoamylcyclohexanol, as an odoriferous or aroma substance, in particular as a flowery odoriferous substance which is distinguished especially by rose and geranium notes, is primarily described. Certain mixtures of cis- and trans-4-isoamylcyclohexanol and a process for the preparation of these mixtures are additionally described.

14 Claims, No Drawings

4-ISOAMYLCYCLOHEXANOL AS ODIFERANT

FIELD OF THE INVENTION

The present invention primarily relates to the use of 4-isoamylcyclohexanol [4-(3-methylbutyl)-cyclohexan-1-ol], in particular of cis-4-isoamylcyclohexanol, as an odoriferous or aroma substance, in particular as a flowery odoriferous substance which is distinguished especially by rose and geranium notes. The invention additionally relates to certain mixtures of cis- and trans-4-isoamylcyclohexanol and a process for the preparation of these mixtures. The present invention furthermore relates to corresponding perfumed products.

BACKGROUND OF THE INVENTION

In the perfume industry there is generally a need for novel and original odoriferous substances, since novel and modern fragrances are constantly to be made available to consumers. Because of the consumer's increasing demand for novel, modern fragrance notes, in the perfume industry there is a constant need for flowery fragrances with which novel effects can be achieved in perfumes and new fashion trends can be created in this manner.

For creation of novel modern compositions, there is a constant need for flowery odoriferous substances having particular olfactory properties which are suitable for serving as a basis for composition of novel, modern perfumes. The odoriferous substances sought should have further notes and aspects, alongside a typical flowery primary smell, which impart to them olfactory character, such as, for example, naturalness and radiance, and complexity.

The search for suitable flowery odoriferous substances which led to the present invention was made difficult by the following circumstances:

The mechanisms of perception of smell are not adequately known.

The relationships between the specific perception of smell on the one hand and the chemical structure of the associated odoriferous substance on the other hand have not been adequately researched.

Slight changes in the structural make-up of a known odoriferous substance often already have the effect of marked changes in the sensorial properties and impair the tolerability for the human organism.

Success in the search for suitable flowery odoriferous substances therefore depends greatly on the intuition of the searcher.

SUMMARY OF THE INVENTION

It was therefore the object of the present invention to discover flowery odoriferous substances having novel olfactory properties, with which particular olfactory notes and aspects can be imparted to odoriferous substance compositions.

It has now been found, surprisingly, that 4-isoamylcyclohexanol is suitable for achieving the object described.

S. Arctander, Perfume and Flavor Chemicals, vol. I and II, Montclair, N.J., 1969, private publishing house, describes the olfactory properties of diverse 4-alkylcyclohexanols. 4-tert-Amylcyclohexanol (number 165) is characterized in its olfactory properties as dry, pine-like woody, with good adhesiveness and considerable diffusivity. Under number 433, the smell of p-tert-butylcyclohexanol is described as extremely dry, woody-camphorous, almost tar-like with leathery aspects. 4-Ethylcyclohexanol (number 1201), on the other hand, has a sweet, quite pungent, gassy smell, accompanied by flowery undertones. Under number 1531, p-heptylcyclohexanol is described as a camphorous-green, partly woody, quite adhesive odoriferous substance. 4-isopropylcyclohexanol (number 2692) is a woody-camphorous, pine-like odoriferous substance with sweet undertones and moderate adhesiveness.

U.S. Pat. Nos. 4,326,997 and 4,400,545 relate to diverse 4-isoamylcyclohexanol derivatives and the use thereof as an olfactory or flavour substance, the 2,6-dimethyl, 2,3,6-trimethyl and 2,3,5,6-tetramethyl derivatives being emphasized in particular. The olfactory properties of all alicyclic 4-isoamylcyclohexanol derivatives, including all the stereoisomers and mixtures thereof (in particular alcohols of the formula (IV) and (VI) and ketones of the formulae (V), (IX) and (X)) are described there globally as balsamic, woody, sweet, root-like, musty, earthy, leathery, citrus-like and herbal. The individual cis and trans isomers were not isolated and characterized.

EP 0 005 198 describes the smell of 4-octylcyclohexanol as weakly woody and slightly flowery.

EP 0 053 979 relates to cyclopentanols and derivatives thereof, in particular 3-alkenylcyclopentan-1-ols and esters thereof. 3-(2-Butenyl/pentenyl)-cyclopentan-1-ols and in particular 1-acetyloxy-3-(2-butenyl)cyclopentane are described as odoriferous substances with rose-like notes.

JP 02-131405 relates to certain insect repellents based on 2-, 3- and 4-alkylcycloalkanols and esters thereof. It is mentioned incidentally, referring to the references in the Arctander monograph already mentioned above, that these insect repellents are harmless to humans, since the compounds employed are suitable as odoriferous substances. No olfactory descriptions are given in the Application itself.

4-Isoamylcyclohexanol is not mentioned.

WO 98/47842 relates, inter alia, to 3-alkylcycloalkanols. The smell of trans-3-isoamylcyclohexan-1-ol is characterized as strong, fatty, grapefruit, rhubarb, lily of the valley, rose and citronellal, whereas that of cis-3-isoamylcyclohexan-1-ol is characterized as weak, very fatty, flowery and nutty. The smell of a mixture of cis- and trans-1-methyl-3-(2-methylpropyl)cyclohexan-1-ol is described as a strongly flowery of the lily of the valley and lilac type, coupled with herbal, pine-like aspects and citrus notes. The pure trans isomer shows, alongside the lily of the valley fragrance, fruity and rhubarb notes, whereas the pure cis isomers in addition have rather herbal and pine-like notes.

The synthesis of 4-isoamylcyclohexanol by hydrogenation of p-isoamylphenol using Raney nickel is described in J. Indian. Chem. Soc. 1956, 33, 313-317. An olfactory description is lacking. Our own experiments have shown that under the experiment conditions stated, a 4-isoamylcyclohexanol having an isomer ratio of cis-:trans-4-isoamylcyclohexanol of about 33:67 is obtained, in this respect, reference is also made to Example 3.1 below.

DETAILED DESCRIPTION OF THE INVENTION

It has now been found, surprisingly, that 4-isoamylcyclohexanol differs significantly in olfactory properties from the structurally related compounds described in the abovementioned documents.

The olfactory description of the isolated cis and trans isomers of 4-isoamylcyclohexanol and of isomers mixtures are shown in Table 1.

TABLE 1

| Compound(s) | Olfactory description |
|---|---|
| cis-4-Isoamylcyclohexanol | strongly rose-like with slight geranium note, very natural, reminiscent of rose oil, clear, transparent, radiant smell, very intensive |
| trans-4-Isoamylcyclohexanol | rose-like, geranium, compared with the pure cis isomer weaker with less radiance and naturalness |
| Mixture comprising 67.6 wt. % cis-4-isoamylcyclohexanol and 31.8 wt. % trans-4-isoamylcyclohexanol | rose-like, animal, natural, indole-like, jasmine, geranium-like, clear, very intensive |
| Mixture comprising 53.9 wt. % cis-4-isoamylcyclohexanol and 44.9 wt. % trans-4-isoamylcyclohexanol | animal, indole-like, flowery, freshly rose-like, geranium-like, very intensive |
| Mixture comprising 33.1 wt. % cis-4-isoamylcyclohexanol and 66.3 wt. % trans-4-isoamylcyclohexanol | rose-like, citronellol-like, indole-like, lilac, skatol, jasmine, flowery, somewhat lily of the valley, less intensive |

The sensorial investigations thus show that 4-isoamylcyclohexanol differs significantly from the sometimes very global indications given in the literature for the sensorial evaluation of structurally related compounds.

Surprising, 4-isoamylcyclohexanol, which was hitherto unknown as an odoriferous substance, differs significantly in its olfactory properties from 3-isoamylcyclohexanol, in particular by the perfumistically sought-after intensive and valuable natural rose and/or geranium note.

In the case of the 4-isoamylcyclohexanol to be employed according to the invention, the cis isomer in particular shows a particularly strongly pronounced smell of roses with a geranium note and a very natural, bright and transparent smell, cis-isoamylcyclohexanol is reminiscent of rose oil and has a high radiance and intensity. One aspect of the present invention therefore relates to (purified) cis-4-isoamylcyclohexanol.

The invention also relates to a mixture (a) comprising or consisting of cis- and trans-4-isoamylcyclohexanol. In this context, according to the invention the weight ratio of cis-4-isoamylcyclohexanol to trans-4-isoamylcyclohexanol is greater than 2:3, preferably greater than or equal to 1:1, particularly preferably greater than or equal to 1.5:1, and especially preferably greater than or equal to 2:1. Preferably, the weight ratio of cis-4-isoamylcyclohexanol to trans-4-isoamylcyclohexanol is less than 6:1, preferably less than 4:1.

A mixture according to the invention of cis- and trans-4-isoamylcyclohexanol has a considerably greater intensity, complexity, radiance, naturalness and elegance compared with the pure cis- or trans-4-isoamylcyclohexanol and is therefore particularly suitable for use in novel and modern perfume compositions.

The inventions furthermore relates to (odoriferous or aroma substance) mixtures comprising or consisting of (b) cis-4-isoamylcyclohexanol and at least one further odoriferous or aroma substance, trans-4-isoamylcyclohexanol not being present, or (c) trans-4-isoamylcyclohexanol and at least one further odoriferous or aroma substance, cis-4-isoamylcyclohexanol not being present.

In mixtures with other odoriferous substances, the 4-isoamylcyclohexanol to be employed according to the invention is already capable in low dosages of increasing the intensity of an odoriferous substance mixture and of rounding off the overall smell of the odoriferous substance mixture, and of imparting to the mixture more radiance and naturalness. In higher dosages, the strong rose-like smell takes effect.

The invention furthermore relates to the use of 4-isoamylcyclohexanol in the form (a) of a mixture of the cis/trans isomers or (b) of cis-4-isoamylcyclohexanol or (c) of trans-4-isoamylcyclohexanol as an odoriferous or aroma substance, in particular the use of a cis/trans isomer mixture in the weight ratios stated above.

A corresponding method of imparting, intensifying or modifying a rose- and/or geranium-like smell comprises the following steps:

provision of 4-isoamylcyclohexanol or a mixture comprising 4-isoamylcyclohexanol, the 4-isoamylcyclohexanol in each case being present in the form (a) of a mixture of the cis/trans isomers or (b) of cis-4-isoamylcyclohexanol or (c) of trans-4-isoamylcyclohexanol, bringing into contact or mixing of a sensorially active amount of the 4-isoamylcyclohexanol or the mixture comprising 4-isoamylcyclohexanol with a product.

The 4-isoamylcyclohexanol can advantageously be prepared from γ,γ-dimethylallyl phenyl ether by rearrangement and subsequent hydrogenation.

γ,γ-Dimethylallyl phenyl ether can be prepared starting from phenol and prenyl chloride in accordance with the instructions according to Helv. Chim. Acta 1968, 1603, in the presence of sodium hydroxide in N-methylpyrrolidone at 45° C., or prepared according to Synthesis, 1998, 256, in the presence of potassium carbonate in acetone.

The γ,γ-dimethylallyl phenyl ether obtainable in this way is then rearranged to 4-(3-methyl-but-2-enyl)-phenol, as described, for example, in Helv. Chim. Acta 1968, 1603, or in J. Org. Chem. 1976, 41, 3026, in the presence of diethylaniline or sodium acetate at 200 to 214° C.

Alternatively, 4-(3-methyl-but-2-enyl)-phenol can also be synthesized by Friedel-Crafts alkylation of phenol and dimethylvinylcarbinol or 3-methyl-but-2-enol in the presence of acids, such as e.g. phosphoric acid. Such a preparation is described in Zh. Org. Khim. (Engl. trans.) 1969, 1027.

The 4-(3-methyl-but-2-enyl)-phenol is then hydrogenated to 4-isoamylcyclohexanol.

The invention also accordingly provides a process for the preparation of 4-isoamylcyclohexanol in the form of a mixture of the cis/trans isomers, having the following step:

hydrogenation of 4-(3-methyl-but-2-enyl)-phenol either (a) in the presence of rhodium or ruthenium, optionally with the addition of an acid, or (b) in the presence of a hydrogenation catalyst of sub-group eight and an acid.

The processes according to the invention differ from the preparation process according to the above-mentioned publication in J. Indian Chem. Soc. in the choice of the catalyst and/or due to the presence of acid. They are suitable for the preparation of the mixtures according to the invention comprising or consisting of cis- and trans-4-isoamylcyclohexanol, the weight ratio of cis-4-isoamylcyclohexanol to trans-4-isoamylcyclohexanol being greater than or equal to 2:3, preferably greater than or equal to 1:1, particularly preferably greater than or equal to 1.5:1, and especially preferably greater than or equal to 2:1.

The catalytic hydrogenation with hydrogen is as a rule carried out according to the invention in the presence of a hydrogenation catalyst of sub-group eight of the periodic table, and preferred hydrogenation catalysts include palladium, nickel, platinum, rhodium or ruthenium, preferably in elemental form. The hydrogenation catalysts employed according to the invention can be applied to organic or inorganic support materials. The hydrogenation catalysts can contain one support material or mixtures of support materials. Advantageous support materials which may be mentioned are active charcoal, charcoal, aluminium oxides, metal oxides, silica gels, zeolites, clays, clay granules or amorphous aluminium silicates. Preferred catalysts are rhodium or ruthenium, and the preferred support material is active charcoal.

The hydrogenation is carried out in accordance with alternative (b) of the process according to the invention with the addition of acids, such as, for example, hydrochloric acid, nitric acid, sulfuric acid, methanesulfonic acid or phosphoric acid, and polymer-supported acids or resins, such as are commercially obtainable, for example, under the names Amberlyst or Lewatit. According to alternative (a) of the process according to the invention—using rhodium or ruthenium as the catalyst—the presence of acid can be omitted. If the hydrogenation is carried out in the presence of an acid, catalytic amounts are advantageous, in particular 0.05 to 20 wt. %, preferably 1 to 15 wt. % of acid, based on 4-(3-methyl-but-2-enyl)-phenol. Advantageous acids are, for example, hydrochloric acid and methanesulfonic acid. The addition of acid during the hydrogenation has the effect in the process alternatives according to the invention of a higher content of cis isomer, which has more valuable olfactory properties.

The weight ratio of the hydrogenation catalyst employed (if applicable: including support material, without water content) to 4-(3-methyl-but-2-enyl)-phenol is preferably in the range of 1:10,000 to 1:10, preferably in the range of 1:1,000 to 1:10 and particularly preferably in the range of 1:100 to 1:20.

The hydrogenation can be carried out in diluents, such as e.g. ethanol, isopropanol, ethyl acetate, hexane, cyclohexane, pentane or heptane, or also without a diluent, i.e. in substance. The diluent-free hydrogenation and the hydrogenation in the diluents hexane or cyclohexane are particularly preferred.

The hydrogenation is typically carried out under a hydrogen pressure in the range of from 1 to 200 bar.

The temperature during the hydrogenation is typically in the range of from 20 to 200° C., preferably in the range of from 70 to 180° C.

The reaction time of the hydrogenation is in many cases advantageously 1 to 50 hours, preferably 2 to 15 hours.

The GC content (content in the gas chromatogram) of the desired 4-isoamylcyclohexanol in the crude product present after the hydrogenation is regularly in the range of from 90 to 100%, taking into account the abovementioned reaction parameters.

The invention also relates to perfumed products comprising a solid or semi-solid carrier and a seasonally active amount, in contact with the solid or semi-solid carrier, of a mixture according to the invention, or a liquid phase and a sensorially active amount of a mixture according to the invention dissolved or suspended therein.

Conventional other perfume constituents with which 4-isoamylcyclohexanol (in each of the forms mentioned, that is to say as the cis isomer, trans isomer or cis/trans isomer mixture) can advantageously be combined to form an odoriferous substance mixture (=perfume oil composition) are to be found e.g. in Steffen Arctander, Perfume and Flavor Chemicals, private publishing house, Montclair, N.J., 1969; K. Bauer, D. Garbe, H. Surburg, Common Fragrance and Flavor Materials, 4th Edition, Wiley-VCH, Weinheim 2001.

There may be mentioned in detail:
extracts from natural raw materials, such as essential oils, concretes, absolutes, resins, resinoids, balsams, tinctures, such as e.g. amber tincture; amyris oil; angelica seed oil; angelica root oil; aniseed oil; valerian oil; basil oil; tree moss absolute; bay oil; artemisia oil; benzoin resin; bergamol oil; beeswax absolute; birch tar oil; bitter almond oil; bean leaf oil; buchu leaf oil; cabreuva oil; cade oil; calamus oil; camphor oil; cananga oil; cardamom oil; cascarilla oil; cassia oil; cassia absolute; castoreum absolute; cedar leaf oil; cedar wood oil; cistus oil; citronella oil: lemon oil, copaiva balsam, copaiva balsam oil; coriander oil; costus root oil; cumin oil; cypress oil; davana oil; dill weed oil; dill seed oil; eau de brouts absolute; oak moss absolute; elemi oil; tarragon oil; Eucalyptus citriodora oil; eucalyptus oil; fennel oil; spruce needle oil; galbanum oil; galbanum resin; geranium oil; grapefruit oil; gualac wood oil; gurjunene balsam; gurjunene balsam oil; helichrysum absolute; helichrysum oil; ginger oil; iris root absolute; iris root oil; jasmine absolute; calamus oil; camomile oil blue; camomile oil Roman; carrot seed oil; cascarilla oil; pine needle oil; spearmint oil; caraway oil; laudanum oil; labdanum absolute; labdanum resin; lavandin absolute; lavandin oil; lavender absolute; lavender oil; lemon grass oil; lovage oil; lime oil distilled; lime oil pressed; linaloa oil; Litsea cubeba oil; bay leaf oil; mace oil; marjoram oil; mandarin oil; massoi bark oil, mimosa absolute; musk seed oil; musk tincture; muscatel sage oil; nutmeg oil; myrrh absolute; myrrh oil, myrtle oil; clove leaf oil; clove blossom oil; neroli oil; olibanum absolute; olibanum oil; opopanax oil; orange blossom absolute; orange oil; oregano oil; palmarosa oil; patchouli oil; perilla oil; Peru balsam oil; parsley leaf oil; parsley seed oil; pelitgrain oil peppermint oil; pepper oil; pimento oil; pine oil; poley oil; rose absolute; rose wood oil; rose oil; rosemary oil; sage oil Dalmatian; sage oil Spanish; sandalwood oil; celery seed oil; spike lavender oil; star aniseed oil; styrax oil; tagetes oil; fir needle oil; lea tree oil; turpentine oil; thyme oil; tolu balsam; tonka absolute; tuberose absolute; vanilla extract; violet leaf absolute; verbena oil; vetiver oil; juniper berry oil; wine yeast oil; wormwood oil; wintergreen oil; ylang oil; hyssop oil; civet absolute; cinnamon leaf oil; cinnamon bark oil; and fractions thereof or constituents isolated therefrom;

individual odoriferous substances from the group consisting of the hydrocarbons, such as e.g. 3-carene; α-pinene; β-pinene; α-terpinene; γ-terpinene; p-cymene; bisabolene; camphene; caryophyllene, cedrene; farnesene; limonene; longifolene; myrcene; ocimene; valencene; (E,Z)-1,3,5-undecatriene;

the aliphatic alcohols, such as e.g. hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2, 6-nonadienol; 3,7-dimethyl-7-methoxyoctan-2-ol; 9-decenol; 10-undecenol; 4-methyl-3-decen-5-ol; the aliphatic aldehydes and 1,4-dioxacycloalken-2-ones thereof, such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal, 2,6,10-trimethyl-5,9-undecadienal; heptanal diethyl acetal; 1,1-dimethoxy-2,2,5-trimethyl-4-hexene; citronellyloxyacetaldehyde;

the aliphatic ketones and oximes thereof, such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; the aliphatic sulfur-containing compounds, such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitrites, such as e.g. 2-nonenoic acid nitrile; 2-tridecenoic acid nitrile; 2,12-tridecenoic acid nitrile; 3,7-dimethyl-2,6-octadienoic acid nitrile; 3,7-dimethyl-6-octenoic acid nitrile;

the aliphatic carboxylic acids and esters thereof, seen as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynate; methyl 2-nonynate; allyl 2-isoamyloxyacetate; methyl 3,7-dimethyl-2,6-octadienoate;

the acyclic terpene alcohols, such as e.g. citronellol, geraniol; nerol; linalool, lavadulol, nerolidol; farnesol; tetrahydrolinalool, tetrahydrogeraniol; 2,6-dimethyl-7-octen-2-ol; 2,6-dimethyloctan-2-ol; 2-methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates; 3-methyl-2-butenoates thereof;

the acyclic terpene aldehydes and ketones, such as e.g. geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

the cyclic terpene alcohols, such as e.g. menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates; 3-methyl-2-butenoates thereof;

the cyclic terpene aldehydes and ketones, such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,8,7,8a-hexahydro-1,1,5,5-tetramethyl-2H-2,4a-methanonaphthalen-8(5H)-one; nootkatone, dihydranootkatone; alpha-sinensal; beta-sinensal and acetylated cedar wood oil (methyl cedryl ketone);

the cyclic alcohols, such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols, such as e.g. alpha,3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers, such as e.g. cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methylpropyl)-1,3-dioxane;

the cyclic ketones, such as e.g. 4-tert-butylcyclohenanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 7-cyclohexadecen-1-one; 8-cyclohexadecen-1-one; 6,7-dihydro-1,1,2,3,3-pentamethyl-4(5H)-indanone; 9-cycloheptadecen-1-one; cyclopentadecanone; cyclohexadecanone;

the cycloaliphatic aldehydes, such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-pentenyl)-3-cyclohexenecarbaldehyde;

the cycloaliphatic ketones, such as e.g. 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols, such as e.g. 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- and -6-indenyl acetate; 4,7-methano-3a,4,5,6,7,7a-hexahydro-5- and -6-indenyl propionate; 4,7-methano-3a,4,5,6,7,7a-hexahydro-5- and -6-indenyl isobutyrate; 4,7-methanooctahydro-5- and 6-indenyl acetate;

the esters of cycloaliphatic carboxylic acids, such as e.g. allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the aromatic hydrocarbons, such as e.g. styrene and diphenylmethane;

the araliphatic alcohols, such as e.g. benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids, such as e.g.: benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; the araliphatic ethers, such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

the aromatic and araliphatic aldehydes, such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenxaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones, such as e.g. acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)-ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof, such as e.g. benzoic acid; phenylacetic acid, methyl benzoate; ethyl benzoate; hexyl benzoate; benzyl benzoate; methylphenyl acetate; ethylphenyl acetate; geranylphenyl acetate; phenylethyl-phenyl acetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds, such as e.g. 2,4,6-trinitro-1,3-dimethyl-5-tert-butylbenzene; 3,5-dinitro-2,6-dimethyl-4-tert-butylacetophenone; cinnamic acid nitrile; 5-phenyl-3-methyl-2-pentenoic acid nitrile; 5-phenyl-3-methylpentanoic acid nitrile; methyl anthranilate; methyl N-methylanthranilate; Schiff's bases of methyl anthranilate with 7-hydroxy-3,7-dimethyloctanal, 2-methyl-3-(4-tert-butylphenyl)propanal or 2,4-dimethyl-3-cyclohexene-carbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

the phenols, phenyl ethers and phenyl esters, such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds, such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones, such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Perfume oils which contain 4-isoamycyclohexanol (in one of the forms mentioned) can be employed for perfumings in liquid form, undiluted or diluted with a solvent. Suitable solvents for this are e.g. ethanol, isopropanol, diethylene glycol monoethyl ether, glycerol, propylene glycol, 1,2-butylene glycol, dipropylene glycol, diethyl phthalate, triethyl citrate, isopropyl myristate etc.

For some uses, it is advantageous to employ perfume oils (odoriferous substance mixtures) containing 4-isoamylcyclohexanol (in one of the forms mentioned) which are adsorbed on a carrier substance, which ensures both a fine distribution of the odoriferous substances in the product and a controlled release during use. Such carriers can be porous inorganic materials, such as light sulfate, silica gels, zeolites, gypsums, clays, clay granules, gas concrete etc., or organic materials, such as woods; cellulose-based substances, sugars or plastics, such as PVC, polyvinyl acetates or polyurethanes.

For other uses, it is advantageous to employ perfume oils comprising 4-isoamylcyclohexanol (in one of the forms mentioned) which are in microencapsulated or spray-dried form or in the form of an inclusion complex or extrusion product and to add them in this form to the precursor/product to be perfumed.

The properties of perfume oils modified in this manner are in some cases optimized further in respect of a more controlled release of fragrance by so-called "coating" with suitable materials, for which purpose waxy plastics, such as e.g. polyvinyl alcohol, are preferably used.

The microencapsulation of the perfume oils can be carried out, for example, by the co-called coacervation process with the aid of capsule materials e.g. of polyurethane-like substances or soft gelatine. The spray-dried perfume oils can be prepared, for example, by spray drying of an emulsion or dispersion containing the perfume oil, it being possible to use modified starches, proteins, dextrin and plant gums as carrier substances. Inclusion complexes can be prepared e.g. by introducing dispersions of the perfume oil and cyclodextrins or urea derivatives into a suitable solvent, e.g. water. Extrusion products can be achieved by melting the perfume oils with a suitable waxy substance and by extrusion with subsequent solidification, optionally in a suitable solvent, e.g. isopropanol.

Perfume oils containing 4-isoamylcyclohexanol (in one of the forms mentioned) can be used in concentrated form, in solutions or in an otherwise modified form for the preparation of e.g. perfume extracts, perfume waters, toilet waters, shaving lotions, cologne waters, pre-shave products, splash colognes and perfumed freshening wipes, as well as perfuming of acid, alkaline and neutral cleaning compositions, such as e.g. floor cleaners, window glass cleaners, dishwashing compositions, bath and sanitary cleaners, scouring milk, solid and liquid WC cleaners, powder and foam carpet cleaners, liquid detergents, pulverulent detergents, laundry pretreatment compositions, such as bleaching compositions, soaking compositions and stain removers, laundry softeners, washing soaps, washing tablets, disinfectants, surface disinfectants and air fresheners in liquid or gelatinous form or in a form applied to a solid carrier, aerosol sprays, waxes and polishes, such as furniture polishes, floor waxes, shoe creams as well as body care compositions, such as e.g. solid and liquid soaps, shower gels, shampoos, shaving soaps, shaving foams, bath oils, cosmetic emulsions of the oil-in-water, of the water-in-oil and of the water-in-oil-in-water type, such as e.g. skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products, such as e.g. hair sprays, hair gels, hair lotions, hair conditioners, permanent and semi-permanent hair colouring compositions, hair setting compositions, such as cold waving compositions and hair straightening compositions, hair waters, hair creams and lotions, deodorants and antiperspirants, such as e.g. underarm sprays, roll-ons, deodorant sticks, deodorant creams or products for decorative cosmetics.

In perfume oil compositions (=odoriferous substance mixtures), the amount of 4-isoamylcyclohexanol (in one of the forms mentioned) employed is conventionally in the range of from 0.001 to 70 wt. %, preferably 0.05 to 50 wt. % and particularly preferably 0.5 to 25 wt. %, based on the total perfume oil composition.

Ingredients with which 4-isoamylcyclohexanol (in one of the forms mentioned) can be combined are, for example:

preservatives, abrasives, anti-acne agents, agents against ageing of the skin, antibacterial agents, anticellulitis agents, antidandruff agents, antiinflammatory agents, irritation-preventing agents, irritation-inhibiting agents, antimicrobial agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, fungicides, gelling agents, gel-forming agents, hair care agents, hair setting agents, hair straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin soothing agents, skin cleansing agents, skin care agents, skin healing agents, skin lightening agents, skin protecting agents, skin softening agents, cooling agents, skin cooling agents, warming agents, skin warming agents, stabilizers, UV-absorbing agents, UV filters, detergents, fabric conditioners, suspending agents, skin tanning agents, thickeners, vitamins, oils, waxes, fats, phospholipids, saturated fatty acids, mono- or polyunsaturated fatty acids, α-hydroxy acids, polyhydroxy-fatty acids, liquefiers, dyestuffs, colour-protecting agents, pigments, anticorrosives, aromas, flavouring substances, odoriferous substances, polyols, surfactants, electrolytes, organic solvents or silicone derivatives.

Odoriferous substance mixtures with a rose-like flowery head note are often sought—in particular for perfuming surfactant-containing formulations, such as, for example, shampoos, detergents or fabric softeners—and these should simultaneously have a pronounced blooming (smell from an aqueous surfactant solution). A further important requirement for the use of odoriferous substance mixtures for surfactant-containing products is their substantivity with respect to or retention on the substrate, in particular hair or textile fibres.

4-Isoamylcyclohexanol is distinguished, in particular for a flowery odoriferous substance, by a high absorption capacity (intrinsic adhesiveness on a substrate) and a high substantivity (ability to be absorbed from a usually aqueous phase on to a substrate and also to remain on a substrate after a washing or rinsing operation. This effect manifests itself in particular on substrates such as skin, hair and textile fibres (e.g. wool, cotton, linen, synthetic fibres).

In direct comparison with the rose-like odoriferous substance cintronellol (3,7-dimethyl-6-octan-1-ol), for example, a significantly higher intrinsic adhesiveness of 4-isoamylcyclohexanol was found. For this, the odoriferous substances were in each case applied as a 5% strength ethanolic solution to a paper odour strip or a cotton strip and smelled at fixed intervals of time.

Surprisingly, when 4-isoamylcyclohexanol (in one of the abovementioned forms) is used according to the invention in a surfactant-containing formulation, a (freshly) rose-like flowery (head) note is achieved not only in combination with a high substantivity/retention, but also in combination with a surprising blooming (which is the smell perceived above a surfactant-containing aqueous solution), interesting jasmine and geranium nuances and indole-like and animal aspects also occurring.

By using 4-isoamylcyclohexanol, as a rule a rose-like flowery note with a pronounced blooming and an increased substantivity for aqueous, surfactant-containing uses can already be achieved in a resulting perfume composition in a low dosage.

Particularly preferred perfumed products according to the invention are therefore detergents and hygiene or care products, in particular in the field of body care, cosmetics and household products.

In addition, odoriferous substances which improve the adhesiveness of the composition (that is to say act as fixatives) or increase the intensity of the olfactory perception (that is to say function as boosters) are of great interest for perfumistic composition.

In addition to the absorption capacity and substantivity, 4-isoamylcyclohexanol is distinguished by its fixing properties. Such a fixative increases the adhesiveness of other odoriferous substances, either by their lowering of vapour pressure or olfactory intensification (e.g lowering of the threshold value). The invention therefore also relates to the use of 4-isoamylcyclohexanol (in one of the abovementioned forms) (as characterized above) as a fixative.

4-Isoamylcyclohexanol (in one of the abovementioned forms) furthermore acts not only as a fixative but also as a so-called booster or enhancer, i.e. it has the effect of intensifying the smell or the olfactory perception of odoriferous substances, odoriferous substance mixtures and perfume compositions. The invention therefore also relates to the use of 4-isoamylcyclohexanol (in one of the abovementioned forms) (as characterized above) as an agent for increasing the olfactory perception of odoriferous substances or odoriferous substance compositions.

The following examples illustrate the invention; unless stated otherwise, contents and percentages relate to the weight.

EXAMPLES

Example 1

Preparation of phenyl prenyl ether
[(3-methyl-but-2-enyloxy)-benzene]

Example 1.1

391 g (4.16 mol) phenol, 532 g (4.16 mol) potassium carbonate and 45 g potassium iodide are initially introduced into 1000 ml acetone. 478 g (4.5 mol) prenyl chloride are added at room temperature. The reaction mixture is then heated under reflux for 4 to 5 hours. When the reaction has ended, the mixture is cooled and water is added. After separation of the phases, the aqueous phase is extracted three times with diethyl ether. The combined organic phases are washed with sodium chloride solution and dried over $Na_2SO_4$, filtered and concentrated. The crude product is purified by distillation. Yield of phenyl prenyl ether: 444 g; 66% of th.

$^1$H-NMR (400 MHz, $CDCl_3$): δ (ppm)=1.74 (d, J=0.9 Hz, 3H), 1.79 (q, J=1.0 Hz, 3H), 4.50 (dt, J=6.82, 0.95 Hz, 2H), 5.50 (d sep., J=6.82, 1.4 Hz, 1H), 6.84-7.04 (m, 3H), 7.22-7.34 (m, 2H).

$^{13}$C-NMR (101 MHz, $CDCl_3$): δ (ppm) 18.28, 25.94, 64.67, 114.66, 119.86, 120.61, 129.44, 137.99, 158.84

Example 1.2

418 g (4.0 mol) prenyl chloride are added dropwise to a stirred mixture of 376.4 g (4.0 mol) phenol and 172 g (4.3 mol) sodium hydroxide in 2,400 g N-methylpyrrolidone at 45° C. in the course of 30 min. The reaction mixture is then subsequently stirred for 1 hour at this temperature. The solid which has precipitated out is filtered off and rinsed with t-butyl methyl ether. The crude product is purified by distillation. Yield of phenyl prenyl ether: 312 g; 83% of th.

Example 2

Rearrangement of phenyl prenyl ether to give 4-(3-methyl-but-2-enyl)-phenol

Example 2.1

837 g (5.16 mol) phenyl prenyl ether and 453 g (5.16 mol) anhydrous sodium acetate are initially introduced into a flask provided with an overhead stirrer in an inert gas atmosphere (nitrogen). The mixture is heated at 190-200° C. for 6 to 8 h, while stirring.

When the reaction has ended, the mixture is cooled and water is added. The phases are then separated and the aqueous phase is extracted three times with 500 ml diethyl ether. The combined organic phases are dried over $Na_2SO_4$, filtered and concentrated on a rotary evaporator. The crude product is purified by distillation. Yield: 413 g; 50% of th.

$^1$H-NMR (400 MHz, $CDCl_3$):δ (ppm)=1.70 (dq, J=1.0. 0.4 Hz, 3H), 1.73 (dq, J=1.1. 0.4 Hz, 3H), 3.26 (d, J=7.4 Hz, 2H), 5.29 (dsep, J=7.4, 1.4 Hz, 1H), 4.70 (s, OH), 6.74-6.80 (m, 2H), 7.0-7.10 (m, 2H).

$^{13}$C-NMR (101 MHz, $CDCl_3$): δ (ppm)=17.72, 25.71, 33.38, 115.22 (2C), 123.46, 129.26 (2C), 132.10. 133.91, 153.12.

Example 2.2

245.8 g (1.5 mol) (3-methylbut-2-enyloxy)benzene and 1,220 ml n diethylaniline are initially introduced into a flask provided with an overhead stirrer. The mixture is heated at 214° C. for 6 h, while stirring.

The mixture obtained in this way is purified by distillation, without working up. Yield: 171 g; 70% of th.

Example 3

Hydrogenation of 4-(3-methyl-but-2-enyl)-phenol to 4-isoamylcyclohexanol

Example 3.1

(Preparation process not according to the invention, J. Indian. Chem. Soc. 1956, 33, 313-317)

165 g 4-(3-methyl-but-2-enyl)-phenol, 2 wt. % Raney nickel-iron (composition of the catalyst: 45% nickel, 3% aluminium, 8% iron; water content 44%) are initially introduced into a stirred autoclave with a gassing stirrer. Hydrogenation is carried out for 6 hours at 170° C. under a hydrogen pressure of 20 bar. After filtration, 165 g of crude product are obtained. 158 g 4-isoamylcyclohexanol (b.p.: 65° C., 0.6 mbar), which has the following composition: 33.1% cis-4-isoamylcyclohexanol and 66.3% trans-4-isoamylcyclohexanol, are obtained by distillation of the crude product.

500 mg (GC purity>98%) of the 4-isoamylcyclohexanol were separated preparatively by means of HPLC. 160 mg cis-4-isoamylcyclohexanol with a GC purity of >98% and 180 mg trans-4-isoamylcyclohexanol with a GC purity of >98% were obtained HPLC conditions: column: Grom Saphir 110 Si, 5 µm, 125×20 mm, eluent: heptene/t-butyl methyl ether (v/v) 60:40, flow rate: 16 ml/min, pressure. 14 bar, temperature: RT detection: RI, additional detection: UV at 210 nm.

cis-4-isoamylcyclohexanol: Assuming that the bulky alkyl radical occupies an equatorial position and the OH group is in the axial position.

$^1$H-NMR (400 MHz, $CDCl_3$): δ (ppm)=0.87 (d, J=6.6 Hz, 6H), 1.15-1.40 (m, 1.66-1.74, 7H), 3.95 (tt, $J_{eq,ax}$=4.7 Hz, J=3.95 Hz, 1H).

$^{13}$C-NMR (101 MHz, $CDCl_3$): δ (ppm)=22.68 (2C), 27.10, 28.23, 32.30, 33.70 (2C), 36.37, 36.46, 67.34.

MS m/z (%): 169 (1[M−H]$^+$), 152 (8 [M−H$_2$O]), 137 (4), 124 (4), 109 (14), 96 (83), 81 (100), 71 (25), 67 (23), 57 (52), 43 (30).

trans-4-isoamylcyclohexanol: Assuming that the bulky alkyl radical occupies an equatorial position and the OH group is in the equatorial position.

$^1$H-NMR (400 MHz, $CDCl_3$): δ (ppm)=0.86 (d, J=6.6 Hz, 6H), 0.90-1.10 (m, 2H), 1.10-1.30 (m, 7H), 1.42-1.52 (m, 2H), 1.72-1.80 (m, 2H), 1.92-2.0 (m, 2H), 3.54 (tt, $J_{ax,ax}$=10.9 Hz, J=4.3 Hz, 1H).

$^{13}$C-NMR (101 MHz, $CDCl_3$): δ (ppm)=22.65 (2C), 28.23, 31.34 (2C), 34.40, 35.65 (2C), 36.52, 36.70, 71.25.

MS m/z (%): 169 (1[M−H]$^+$), 152 (11 [M−H$_2$O]), 137 (5), 124 (4), 109 (16), 96 (99), 81 (100), 71 (46), 67 (32), 57 (76), 43 (44).

Example 3.2

330 g 4-(3-methyl-but-2-enyl)-phenol, 3 wt. % ruthenium-on-active charcoal (Ru content, based on the weight of the dry catalyst: 5%; water content about 50%) are initially introduced into 570 ml isopropanol in a stirred autoclave with a gassing stirrer. Hydrogenation is carried out for 5 hours at 100° C. under a hydrogen pressure of 130 bar. After filtration, 329 g 4-isoamylcyclohexanol are obtained as a crude product. After distillation, 316 g 4-isoamylcyclohexanol, which has the following composition: 53.8% cis-4-isoamylcyclohexanol and 44.9% trans-4-isoamylcyclohexanol, are obtained.

Example 3.3

85 g 4-(3-methyl-but-2-enyl)-phenol, 3 wt % rhodium-on-active charcoal (Rh content, based on the weight of the dry catalyst: 5%; water content about 50%) are initially introduced into 500 ml isopropanol and 9.6 g methanesulfonic acid in a stirred autoclave with a gassing stirrer. Hydrogenation is carried out for 5 hours at 80° C. under a hydrogen pressure of 10 bar. After filtration, 85 g 4-isoamylcyclohexanol are obtained as a crude product. After distillation, 80 g 4-isoamylcyclohexanol, which has the following composition: 67.6% cis-4-isoamylcyclohexanol and 31.8% trans-4-isoamylcyclohexanol, are obtained.

Example 3.4

85 g 4-(3-methyl-but-2-enyl)-phenol, 3 wt. % rhodium-on-active charcoal (Rh content, based on the weight of the dry catalyst: 5%; wafer content about 50%) are initially introduced into 300 ml cyclohexane in a stirred autoclave with a gassing stirrer. Hydrogenation is carried out for 5 hours at 100° C. under a hydrogen pressure of 20 bar. After filtration, 85 g 4-isoamylcyclohexanol are obtained as a crude product. After distillation, 80 g 4-isoamylcyclohexanol, which has the following composition: 50.4% cis-4-isoamylcyclohexanol and 49.1% trans-4-isoamylcyclohexanol, are obtained.

Smell: Freshly rose-like, intensive, flowery, geranium-like, indole-like, animal.

Example 4

Preparation of a perfume oil having a modern, distinctly flowery rose-like note.

The following odoriferous substances are mixed in the stated amounts (parts by weight):

| | |
|---|---|
| Ethyl acetate | 13 |
| Hexenyl acetate, cis-3- | 1.5 |
| Vertocitral, Symrise | 1 |
| Hexenol, cis-3- | 0.5 |
| Isoananate, Symrise | 5 |
| Styrenyl acetate | 8 |
| Leguminal, Symrise | 0.2 |
| Dihydromyrcenol | 11 |
| Mandarin oil | 5 |
| Menthol l-, Symrise | 3 |
| Aldehyde C14 so-called | 1 |
| Lilial, Givaudan | 65 |
| Bourgeonal, Quest | 3 |
| Hellonal, IFF | 3 |
| Florhydral, Givaudan | 10 |
| Mugetanol, Symrise | 50 |
| Lyral, IFF | 57 |
| Ethyllinalool, Givaudan | 102 |
| Dimethylbenzylcarbinyl acetate | 3 |
| Phenylethyl alcohol | 20 |
| Geraniol | 10 |
| Citronellol | 18 |
| Citronellyl acetate | 7 |
| Geranyl acetate | 4 |
| Damascone alpha, Firmenich | 0.5 |
| Benzyl acetate | 14 |
| Methyl dihydrojasmonate | 158 |
| Hexenyl salicylate, cis-3- | 4 |
| Iraldein gamma, Symrise | 7 |
| Coumarin | 0.3 |
| Iso E Super, IFF | 18 |
| Patchouli oil | 4 |
| Sandolen, Symrise | 3 |
| Ambroxide cryst., Symrise | 1 |
| Globalid, Symrise | 18 |
| Ethylene brassylate | 21 |
| Total | 650 |

This starting composition is a perfume oil with a green, flowery accord with a distinct lily of the valley and rose note.

By addition of 100 parts by weight of 4-isoamylcyclohexanol (from Example 3.4) to 650 parts by weight of the starting composition, a modern perfume with a pronounced fanciful rose note is obtained. Compared with the starting composition, the odoriferous substance composition according to the invention comprising 4-isoamylcyclohexanol has a finer, flowery rose-like, harmonious and rounded-off smell. The radiance and spatial effect of the starting composition are increased considerably by the addition of 4-isoamylcyclohexanol.

Examples 5 to 7

Comparison Examples

In the comparison experiments described in the following, a cis/trans-4-isoamyl alcohol isomer mixture (composition according to Example 3.2) according to the invention was tested in comparison with citronellol, which is not according to the invention, in various hygiene and washing products, both by several experts and by a group of 16 lay testers, and considerably olfactory differences were thereby found.

Example 5

Washing Powder (Powder Detergent)

In each case 80 g of washing powder (composition: 9% $C_{12}$-$C_{13}$ linear Na alkylbenzenesulfonates, 1.6% $C_{14}$-$C_{15}$ Na alkylethoxy-sulfate (EO=0.6), 5.7% $C_{12}$-$C_{18}$ alkyl-sulfates, 3.3% polyacrylate (MW=4,500), 27% aluminosilicate, 0.6% sodium silicate, 28% sodium carbonate, 9% sodium sulfate, 0.2% optical brightener, 1.8% polyethylene glycol (MW=4,000), 1% perborate, 1.1% enzymes (lipase, protease, cellulase), water q.s.) were mixed with 1 g of a 50% strength solution in isopropyl myristate of (a) a 4-isoamylcyclohexanol mixture according to the invention or (b) citronellol, and the washing powders were stored at room temperature for 24 hours. In each case two hand towels of cotton and two hand towels of blended fabric were then washed separately with the 80 g portions of washing powder at 40° C. in washing machines (manufacturer: Miele).

The damp laundry obtained in this way was investigated tor its olfactory properties, and it was found that the 4-isoamylcyclohexanol mixture according to the invention had a significantly higher fragrance intensity.

In conclusion, the individual hand towels were dried on a line for 24 hours. The perfumistic evaluation of the two hand towels by a group of experts gave a significantly higher fragrance intensify for the 4-isoamylcyclohexanol mixture according to the invention. In a blindfold evaluation, a group of testers comprising 16 lay testers clearly preferred the hand towels with the 4-isoamylcyclohexanol mixture according to the invention with a significant difference (p<0.05).

Example 6

Fabric Softener

In each case 40 g of a fabric softener (3-times concentrate, 94% drinking water, 5.5% quaternary ethanolamine ester (ester-quats; quaternary ammonium methosulfate). 0.2% alkyldimethylbenzylammonium chloride (Preventol® R50, Bayer AG) and 0.3% of a blue dyestuff solution) were mixed thoroughly with 0.5 g of a 50% strength solution in isopropyl myristate of (a) a 4-isoamylcyclohexanol mixture according to the invention or (b) citronellol, and the fabric softeners were stored for 24 h at room temperature. The pH of the fabric softener concentrate is typically in the range of 2-3. In each case three hand towels of cotton and three hand towels of blended fabric were then washed at 40° C. in washing machines (manufacturer: Miele) first with 80 g of a non-perfumed standard washing powder and subsequently separately with the fabric softeners to be investigated.

The damp laundry obtained in this way was dried on a line for 24 hours. The olfactory evaluation of the dry hand towels showed that the 4-isoamylcyclohexanol mixture according to the invention had a significantly higher fragrance intensity.

The following table shows the results for the intensity and the preference according to the particular evaluation of the dry hand towels after treatment with the respective fabric softeners, in each case on a scale of from 1 (=very weak or not pleasant) to 6 (=very intense or very pleasant). In both cases, the statistical evaluation was significant (p<0.05).

| Mixture | Intensity | Preference |
| --- | --- | --- |
| 4-Isoamylcyclohexanol | 3.0 | 3.7 |
| Citronellol | 2.6 | 3.0 |

Example 7

Shampoo

In each case 30 g of a shampoo (20% Plantacare® PS 10 (Cognis GmbH, Na laureth sulfate and lauryl glycoside), 2% sodium chloride, 1.3% citric acid, 0.5% Dragocid® Liquid (Symrise GmbH & Co. KG, mixture of phenoxyethanol and methyl-, ethyl-, propyl- and butylparaben), 76.2% water) were mixed thoroughly with 0.3 g of a 50% strength solution in isopropyl myristate or (a) a 4-isoamylcyclohexanol mixture according to the invention and (b) citronellol, and the shampoos were stored for 24 hours at room temperature. The pH of the shampoo was about 6. In each case a 20 g hank of hair (real hair) was then washed separately by hand for 1 minute with 1 g of the particular shampoos, which was foamed in 2 g of water. Finally, the two hanks of hair were rinsed separately under 30° C. hot wafer for 30 seconds.

The damp hanks of hair obtained in this way were dried for 1 minute with an electric hair dryer on the middle setting. The olfactory evaluation of the hanks of hair showed that the 4-isoamylcyclohexanol mixture according to the invention was both perceived to be more intense on damp and dry hair and preferred in its olfactory properties.

The following table shows the results for the intensity and the preference according to the particular evaluation of the dry and damp hanks of hair after treatment with the fabric softeners, in each case on a scale of from 1 (=very weak or not pleasant) to 6 (=very intense or very pleasant. In all cases, the statistical evaluation was highly significant (p<0.01).

| Mixture | Damp hanks of hair | | Dry hanks of hair | |
| --- | --- | --- | --- | --- |
| | Intensity | Preference | intensity | Preference |
| 4-Isoamylcyclohexanol | 3.0 | 3.6 | 2.3 | 3.8 |
| Citronellol | 2.8 | 3.0 | 2.0 | 3.1 |

We claim:

1. A composition comprising greater than 98 wt-% cis-4-isoamylcyclohexanol.

2. A mixture comprising
   (a) cis-4-isoamylcyclohexanol and trans-4-isoamylcyclohexanol, the weight ratio of cis-4-isoamylcyclohexanol to trans-4-isoamylcyclohexanol being greater than 2:3, or
   (b) greater than 98 wt-% cis-4-isoamylcyclohexanol based on the total amount of 4-isoamylcyclohexanol and at least one further odoriferous or aroma substance, or
   (c) greater than 98 wt-% trans-4-isoamylcyclohexanol based on the total amount of 4-isoamylcyclohexanol and at least one further odoriferous or aroma substance.

3. A perfumed product comprising a sensorially active amount of a mixture according to claim 2 and
   (a) a solid or semi-solid carrier in contact with said mixture, or
   (b) a liquid phase dissolved or suspended therein.

4. A perfumed product according to claim 3, wherein the product is a detergent or a hygiene or care product.

5. The mixture according to claim 2, comprising
   (a) cis-4-isoamylcyclohexanol and trans-4-isoamylcyclohexanol, the weight ratio of cis-4-isoamylcyclohexanol to trans-4-isoamylcyclohexanol being greater than 2:3, or
   (b) cis-4-isoamylcyclohexanol and at least one further odoriferous or aroma substance, trans-4-isoamylcyclohexanol not being present, or
   (c) trans-4-isoamylcyclohexanol and at least one further odoriferous or aroma substance, cis-4-isoamylcyclohexanol not being present.

6. A method of imparting an odor or aroma to a substance by contacting said substance with 4-isoamylcyclohexanol in the form of
   (a) a mixture of the cis/trans isomers in a ratio greater than 2:3 by weight, or
   (b) greater than 98 wt-% cis-4-isoamylcyclohexanol based on the total amount of 4-isoamylcyclohexanol, or
   (c) greater than 98 wt-% trans-4-isoamylcyclohexanol based on the total amount of 4-isoamylcyclohexanol.

7. The method according to claim 6, wherein said 4-isoamylcyclohexanol is in the form of
   (a) cis-4-isoamylcyclohexanol and trans-4-isoamylcyclohexanol, the weight ratio of cis-4-isoamylcyclohexanol to trans-4-isoamylcyclohexanol being greater than 2:3, or
   (b) cis-4-isoamylcyclohexanol, with trans-4-isoamylcyclohexanol not being present, or
   (c) trans-4-isoamylcyclohexanol, with cis-4-isoamylcyclohexanol not being present.

8. The method according to claim 7, further comprising contacting said substance with at least one further odoriferous or aroma substance.

9. A method for imparting, intensifying or modifying a rose and/or geranium-like smell comprising:

provilding 4-isoamylcyclohexanol or a mixture comprising 4-isoamylcyclohexanol in the form of
- (a) a mixture of the cis/trans isomers in a ratio greater than 2:3 by weight, or
- (b) greater than 98 wt-% cis-4-isoamylcyclohexanol based on the total amount of 4-isoamylcyclohexanol, or
- (c) greater than 98 wt-% trans-4-isoamylcyclohexanol based on the total amount of 4-isoamylcyclohexanol; and bringing into contact or mixing of a sensorially active amount of the 4-isoamylcyclohexanol or the mixture comprising 4-isoamylcyclohexanol with a product.

10. The method according to claim 9, wherein said 4-isoamylcyclohexanol or mixture comprising 4-isoamylcyclohexanol is in the form of:
- (a) cis-4-isoamylcyclohexanol and trans-4-isoamylcyclohexanol, the weight ratio of cis-4-isoamylcyclohexanol to trans-4-isoamylcyclohexanol being greater than 2:3, or
- (b) cis-4-isoamylcyclohexanol, with trans-4-isoamylcyclohexanol not being present, or
- (c) trans-4-isoamylcyclohexanol, with cis-4-isoamylcyclohexanol not being present.

11. The method according to claim 10, wherein said 4-isoamylcyclohexanol or mixture comprising 4-isoamylcyclohexanol comprises at least one further odoriferous or aroma substance.

12. A method for increasing the olfactory perception of odoriferous substances or odoriferous substance compositions by adding 4-isoamylcyclohexanol as a fixative or as an agent in the form of
- (a) a mixture of the cis/trans isomers in a ratio greater than 2:3 by weight, or
- (b) greater than 98 wt-% cis-4-isoamylcyclohexanol based on the total amount of 4-isoamylcyclohexanol, or
- (c) greater than 98 wt-% trans-4-isoamylcyclohexanol based on the total amount of 4-isoamylcyclohexanol.

13. The method according to claim 12, wherein said 4-isoamylcyclohexanol is in the form of:
- (a) cis-4-isoamylcyclohexanol and trans-4-isoamylcyclohexanol, the weight ratio of cis-4-isoamylcyclohexanol to trans-4-isoamylcyclohexanol being greater than 2:3, or
- (b) cis-4-isoamylcyclohexanol, with trans-4-isoamylcyclohexanol not being present, or
- (c) trans-4-isoamylcyclohexanol, with cis-4-isoamylcyclohexanol not being present.

14. The method according to claim 13, further comprising adding at least one further odoriferous or aroma substance to said odoriferous substance or odoriferous substance composition.

* * * * *